United States Patent
Thaung

(10) Patent No.: US 9,545,198 B2
(45) Date of Patent: Jan. 17, 2017

(54) GUIDE STAR GENERATION

(71) Applicant: Profundus AB, Sollentuna (SE)

(72) Inventor: Jorgen Thaung, Molndal (SE)

(73) Assignee: PROFUNDUS AB, Sollentuna (SE)

( * ) Notice: Subject to any disclaimer, the term of this patent is extended or adjusted under 35 U.S.C. 154(b) by 50 days.

(21) Appl. No.: 14/396,301

(22) PCT Filed: Apr. 17, 2013

(86) PCT No.: PCT/EP2013/057994
§ 371 (c)(1),
(2) Date: Oct. 22, 2014

(87) PCT Pub. No.: WO2013/160171
PCT Pub. Date: Oct. 31, 2013

(65) Prior Publication Data
US 2015/0085255 A1 Mar. 26, 2015

(30) Foreign Application Priority Data
Apr. 24, 2012 (EP) .................................... 12165365

(51) Int. Cl.
*G01J 9/00* (2006.01)
*A61B 3/10* (2006.01)
(Continued)

(52) U.S. Cl.
CPC .............. *A61B 3/1015* (2013.01); *A61B 3/103* (2013.01); *G01J 1/0411* (2013.01); *G01J 3/0208* (2013.01); *G01J 9/00* (2013.01)

(58) Field of Classification Search
CPC .......... A61B 3/1015; A61B 3/103; G01J 9/00; G01J 1/0411; G01J 3/0208
(Continued)

(56) References Cited

U.S. PATENT DOCUMENTS 6,278,100 B1 * 8/2001 Friedman ............... G01C 11/00
250/201.9
6,550,917 B1 * 4/2003 Neal ...................... A61B 3/158
351/221
(Continued)

OTHER PUBLICATIONS

PCT International Search Report mailed Jul. 19, 2013 for PCT International Application No. PCT/EP2013/057994, 2 pages.

*Primary Examiner* — Bumsuk Won
*Assistant Examiner* — William R Alexander
(74) *Attorney, Agent, or Firm* — Remarck Law Group PLC

(57) ABSTRACT

An optical system (120) for detecting optical aberrations of light from an object (101), the optical system comprising: a reference light-source (102) providing collimated reference light; an optical element (212) configured to focus at least one collimated light beam incident on the optical element (212) to a plurality of focal points in a conjugate object plane (214), the optical element (212) being arranged in an optical path between the reference light-source (102) and the object (101) for transmitting a plurality of reference light beams towards the object (101); and a wavefront sensor (112) configured to detect a property indicative of an optical aberration of light incident on the wavefront sensor; wherein the optical element (212) is further arranged to transmit a plurality of reflected guide star light beams resulting from reflection of the reference light beams at the object (101) towards the wavefront sensor (112).

11 Claims, 3 Drawing Sheets

(51) Int. Cl.
*G01J 3/02* (2006.01)
*G01J 1/04* (2006.01)
*A61B 3/103* (2006.01)

(58) Field of Classification Search
USPC ............... 351/200, 205, 618, 619, 629, 637
See application file for complete search history.

(56) References Cited

U.S. PATENT DOCUMENTS

| | | | |
|---|---|---|---|
| 6,634,750 | B2 | 10/2003 | Neal et al. |
| 8,009,280 | B1 * | 8/2011 | Erry .......................... G01J 9/00 351/205 |
| 8,087,779 | B2 | 1/2012 | Levecq |
| 2002/0097376 | A1 | 7/2002 | Applegate et al. |
| 2007/0229993 | A1 * | 10/2007 | Hemmati ............... G02B 23/06 359/846 |
| 2007/0236701 | A1 * | 10/2007 | Neal .................... A61B 3/1005 356/512 |
| 2007/0247638 | A1 * | 10/2007 | Owner-Petersen .... A61B 3/156 356/511 |

* cited by examiner

GUIDE STAR GENERATION

CROSS-REFERENCE TO RELATED APPLICATIONS

This application is a 371 U.S. National Stage of International Application No. PCT/EP2013/057994, filed Apr. 17, 2013, which claims priority to EPC No. 12165365.3, filed Apr. 24, 2012. The disclosure of each of the above applications is incorporated herein by reference in their entirety.

FIELD OF THE INVENTION

The present invention relates to an optical system for detecting optical aberrations introduced by turbulent or aberrated media between an object of interest and a detector.

TECHNICAL BACKGROUND

In optical imaging systems it may be necessary to correct for optical aberrations, or phase errors, that blur the image of an object under observation. Typical applications where such correction is required are e.g. ground based telescopes, where the image of an observed object is blurred by the atmosphere, and retinal imaging, where the image of the retina is blurred by the eye's optical aberrations.

One way to correct for such aberrations is to use an adaptive optics (AO) system. Adaptive optics has been applied in different areas of science and industry, e.g. to enhance the capabilities of imaging systems in astronomy, microscopy, and ophthalmology, to enhance signal quality in optical communication systems, and also in laser beam control. In environments where an imaging system is used to observe objects behind a continuously evolving phase curtain (atmosphere, ocular optics, heating effects, etc.), the adaptive optics system can effectively mitigate the effects of this medium to regain the loss of imaging performance.

In systems using adaptive optics, a Shack-Hartmann wavefront sensor may be used to detect an optically aberrated wavefront. A Shack-Hartmann sensor usually makes use of a point source having a known position, a so-called guide star, located somewhere within the field of view to be imaged. By sampling the wavefront of the guide star image, and comparing the acquired samples with known reference samples, it is possible to determine the aberration of a wavefront. Furthermore, it is possible to measure aberrations over a larger field of view by using multiple guide stars.

Once the optical aberrations are known, the AO-system may correct the aberrated wavefront by using one or more wavefront modifying devices, e.g. deformable mirrors or reflective or transmissive phase modulators.

However, with the use of multiple guide stars, it is increasingly important to accurately align the guide star source with various optical elements in the optical system. A system using multiple guide stars thereby becomes more sensitive to misalignment of optical elements, which may for example occur through mechanical movement or through thermal expansion.

In U.S. Pat. No. 6,634,750, a plurality of guide stars is formed by using an array of light-sources to provide a plurality of light beams, each representing a guide star. Each point source in the array provides a collimated light beam which passes through a common lens in order to provide a set of collimated beams at different angles. As the collimated beams are diverging, it is critical that the following optical elements, such as lenses and apertures, are correctly positioned, as any misalignment will lead to subsequent errors in the detection system.

Accordingly, there is a need for a more robust optical system using multiple guide stars and a wavefront sensor to detect optical aberrations.

SUMMARY OF THE INVENTION

In view of the aforementioned and other drawbacks of prior art, a general object of the present invention is to provide an improved optical system for creating guide stars and detecting optical aberrations that is more robust and that also offers improved flexibility.

According to a first aspect of the present invention, an optical system is provided for detecting optical aberrations of light from an object, the optical system comprising: a reference light-source providing collimated reference light, an optical element configured to focus at least one collimated light beam incident on the optical element to a plurality of focal points in a conjugate object plane, the optical element being arranged in an optical path between the reference light-source and the object for transmitting a plurality of reference light beams towards the object, and a wavefront sensor configured to detect a property indicative of an optical aberration of light incident on the wavefront sensor, wherein the optical element is further arranged to transmit a plurality of reflected guide star light beams resulting from reflection of the reference light beams at the object towards the wavefront sensor.

The object at which light is reflected may be different depending on the field of application. In the field of ophthalmology, the object may typically be the retina. In the field of astronomy, guide stars may be formed through reflection of a reference light beam by the atmosphere.

A conjugate plane of a given plane, P, is a plane P' such that points on P are imaged at P'.

Furthermore, a collimated light beam should in the present context be understood as light propagating, at least locally, in the form of an essentially plane wave.

The wavefront sensor may be any sensor capable of detecting phase aberrations of light reaching the sensor. For example, a Shack-Hartmann-type sensor comprising a lenslet array and an imaging device such as a CCD or CMOS sensor may be used. Each lens of the lenslet array samples the wavefront, and focuses the light reaching each lenslet on the imaging device. By comparing the position of the resulting focus point of each lenslet with a known reference position, the local tilt of a wavefront reaching the sensor can be determined, thereby allowing an approximation of the phase aberration of the wavefront.

The reference light-source should be understood as a lighting device providing at least one collimated reference light beam.

The present invention is based on the realization that an optical system for detecting optical aberrations may be improved by arranging an optical element such that light passes the optical element both on the way from the reference light-source to the object and on the way from the object to the wavefront sensor. Thereby, the optical system acts as an auto-collimating system, in the sense that collimated light from the reference light-source that passes the optical element is reflected back from the object to the same optical element.

The optical element is asymmetric so that collimated light reaching the optical element from a first direction is focused to a plurality of focal points and the reflected guide star light beams reflected at the object reaching the optical element from a second direction are transmitted from the optical element as collimated light.

An advantage achieved through various embodiments of the present invention is that complicated alignment of the reference light-source and the optical element can be avoided due to the auto-collimation provided by the setup. As the light propagating from the reference light-source to the optical element, and the light propagating from the optical element towards the wavefront sensor, is collimated, the distance between optical components is not as critical as if the light would be non-collimated (as in the optical system according to U.S. Pat. No. 6,634,750). Thereby, the optical system according to various embodiments of the present invention is more robust in that it is less sensitive to misalignment of various elements in the system.

Furthermore, as the reflected guide star light beams are collimated following passage through the optical element, they reach the lenslet array of the wavefront sensor as an essentially plane wave. Hence, by controlling the diameter of the reflected guide star light beams as they reach the lenslet array, each beam will only reach a certain number of the lenslets resulting in that the Hartmann patterns for each of the reference beams are separated. Thereby, further analysis is simplified.

An additional advantage achieved through various embodiments of the present invention is that the configuration of reference light beams may be changed simply by changing the configuration of the optical element. This may for example be done by exchanging the optical element or by rearranging parts of the optical element. Hereby, a more flexible optical system is provided where the configuration of guide stars on the object may be easily changed to provide essentially any desirable guide star pattern.

According to one embodiment of the invention, the optical system may advantageously comprise a focusing lens, a field stop, and a collimating lens, wherein the focusing lens is configured to focus a plurality of reflected guide star light beams transmitted through the optical element to a focal point located at the opening of the field stop, and wherein the collimating lens is arranged between the field stop and the wavefront sensor and configured to collimate the reflected guide star light beams propagating from the opening in the field stop towards the wavefront sensor. A field stop should in the present context be understood as an aperture through which the light beam may travel.

It is desirable to reduce the amount of light reaching the wavefront sensor coming from stray light or parasitic source reflections. The aforementioned arrangement reduces the amount of stray light reaching the wavefront sensor.

In one embodiment of the invention, the field stop may advantageously be arranged in optical conjugate plane to the reference light-source plane. In this embodiment, the reference light is generated (by the reference light-source) and spatially filtered (by the field stop) in virtually the same point. This means that the returning guide star light beams will all automatically pass through the field stop without cumbersome and time consuming alignment and adjustment.

According to one embodiment of the invention the optical element may be a phase modulating device, such as a spatial light modulator, an acousto-optic modulator, or a plurality of off-axis parabolic mirrors.

According to one embodiment of the invention, the optical element may advantageously be a collimating lens array (CLA) comprising a plurality of similar lenses arranged in the same plane and having the same focal length. Here, the focal points are located in a plane conjugate to the object plane. The configuration of the lenses in the CLA may be arbitrarily chosen in order to provide any desirable configuration of reference light beams and consequently guide star light beams. However, the optical element may be a single element comprising separate focusing regions in order to create a number of focal points in the same plane.

A more detailed description of a multi-object wavefront sensor using a CLA and a field stop may be found in U.S. Pat. No. 7,639,369, which is hereby incorporated by reference in its entirety.

In one embodiment of the invention, the reference light-source may comprise a light emitting device and a collimating lens for collimating the light provided by the light emitting device. Using a collimating lens to collimate light emitted by the light emitting device offers a greater flexibility in the choice of light emitting device as it allows the use of light emitting devices emitting non-collimated light.

Furthermore, the light emitting device may advantageously be a point light-source. The point light-source may e.g. be a superluminescent diode, a light emitting diode, a laser diode, or the end of an optical fiber light-guide.

Furthermore, the reference light-source may advantageously comprise a pupil mask comprising a plurality of openings configured to transform light from a light-source into a plurality of reference light beams. As described above, the optical element may transform a collimated light beam into a plurality of reference light beams. However, by using a pupil mask in the reference light-source a plurality of collimated light beams may be formed prior to reaching the optical element. Thus, the light beams reaching the optical element may have the same configuration as the optical element, thereby avoiding artefacts and undesirable reflections from the optical element.

According to various embodiments of the invention, the optical system may further comprise a light redirecting device arranged between the optical element and the wavefront sensor and configured to direct the collimated reference light from the reference light-source towards the optical element, and to allow passage of the reflected guide star light beams transmitted from the optical element towards the wavefront sensor. The light redirecting device is thus arranged so that the reference light-source may be placed in a light path separate from the light path between the optical element and the wavefront sensor. The light redirecting device may for example be a static device such as a beam splitter. However, dynamic light redirection or routing achieved by a controllable beam deflection device such as an optical switch or any other suitable optical element may equally well be used. In the case of dynamic routing, a light beam incident on the beam splitting device may be controlled to alternatingly be redirected and transmitted.

According to one embodiment of the invention, the optical system may further comprise a first polarizing filter arranged between the reference light-source and the light redirecting device such that light passing the first polarizing filter has a first polarization, and a second polarizing filter arranged between the light redirecting device and the wavefront sensor, wherein the second polarizing filter is configured so that passage of light having the first polarization is blocked. Alternatively, a light-source emitting first polarized light can be used, and a polarizing filter arranged between the light redirecting device and the wavefront sensor is configured so that passage of light having the first polarization is blocked.

As mentioned above, it is desirable to reduce the amount of light reaching the wavefront sensor coming from parasitic source reflections. If such undesirable reflections were to reach the wavefront sensing device, they would interfere with the reflected guide star light beams coming from the object, thus making wavefront detection more difficult. Such undesirable reflections may be avoided by arranging polarizing filters in the aforementioned manner. For example, if linear polarizing filters are used, the two filters may be rotated 90° in relation to each other so that the first filter provides linear polarized light which is then blocked by the second polarizer. Alternatively, circular polarizing filters or a combination of linear and circular polarizing filters may be used. The aforementioned arrangement may advantageously be used if light becomes depolarized or changes polarization on the light-path between the optical element and the object either in the direction to or from the object. In the case where the object is a retina, a majority of the light reflected at the retina is depolarized, thus allowing the described arrangement of polarizing filters.

According to one embodiment of the invention, the optical system may further comprise at least one wavefront modifying device arranged between the optical element and the object. An optical system comprising a wavefront modifying device is commonly known as an adaptive optics (AO) system having adaptive capabilities for compensating for static and/or non-static optical aberrations introduced by the medium between an object and a detecting device. Furthermore the wavefront modifying device should be understood as any device that is controllable to modify the wavefront (spatial phase distribution) of light. Examples of such wavefront modifying devices include e.g. deformable mirrors, spatial light modulators, etc.

The optical system according to various embodiments of the invention may for example be provided in an adaptive optical system for compensating for optical aberrations further comprising: a control system; the optical system configured to provide an input signal to the control system corresponding to an optical aberration of received light detected by the optical system; an image detecting device configured to provide an input to the control system; a second beam splitting device arranged between the optical system and an object, configured to redirect a portion of received light towards the image detecting device; and a wavefront modifying device controlled by the control system and arranged between the second beam splitting device and the object; wherein the control system is configured to control the wavefront modifying device based on the input signal from the optical system.

Further features of, and advantages with, the present invention will become apparent when studying the appended claims and the following description. The skilled person realize that different features of the present invention may be combined to create embodiments other than those described in the following, without departing from the scope of the present invention.

BRIEF DESCRIPTION OF THE DRAWINGS

These and other aspects of the present invention will now be described in more detail with reference to the appended drawings showing an example embodiment of the invention, wherein.

DETAILED DESCRIPTION OF EXAMPLE EMBODIMENTS OF THE INVENTION

In the present detailed description, various embodiments of an optical system for detecting optical aberrations according to the present invention are mainly discussed with reference to an adaptive optics system for detecting optical aberrations of light reflected by a retina within the field of ophthalmology. In the following embodiment, a point source is used to generate a reference light beam, and an image detecting device is provided in the form of an image sensor, which is used to acquire pixelated images of the object. Furthermore, one or more so-called guide stars are described as being generated by the adaptive optics system.

Figure 1:
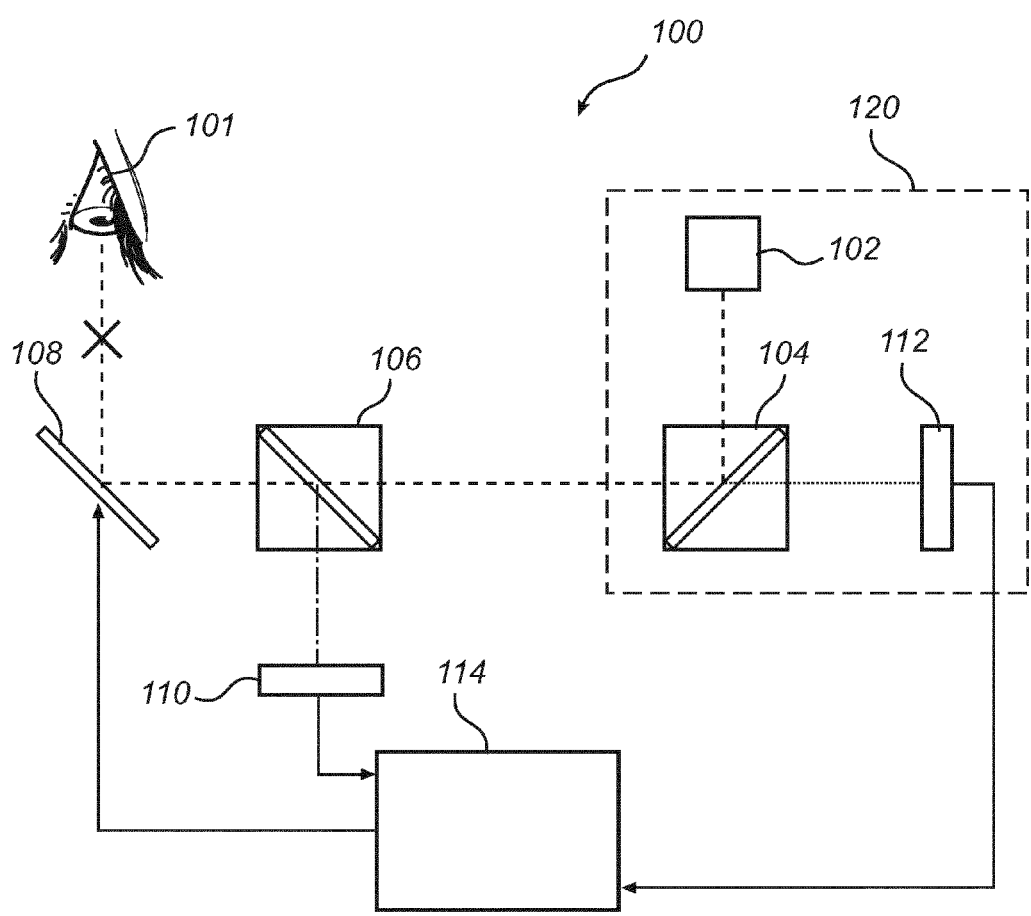
FIG. 1 schematically illustrates an optical system according to an embodiment of the present invention.

FIG. 1 schematically shows an adaptive optical system 100 according to an embodiment of the present invention for detecting optical aberration of light reflected at an object 101, here the object is the retina of an eye 101. The adaptive optical system 100 in FIG. 1 comprises a reference light-source 102, a first beam splitting device 104 in the form of a pellicle beam splitting device 104, a second beam splitting device 106, a wavefront modifying device 108, a detecting device 110, a wavefront sensor 112, and a control system 114. The detecting device 110 and the wavefront sensor 112 are connected to the control system 114. The control system 114 is further connected to the wavefront modifying device 108 and configured so that, when in operation, the adaptive optical system 100 in FIG. 1 corrects for time-varying aberrations between the object 101 and the wavefront sensor 112 by regulating the wavefront modifying device 108 based on wavefront measurements from the wavefront sensor 112.

In the adaptive optical system 100, light emitted by the reference light-source 102 is directed by the first beam splitting device 104 towards the object 101 through the second beam splitting device 106 and via the wavefront modifying device 108. Light reflected at the object 101 returns along the same path via the wavefront modifying device 108 through the second beam splitting device 106 towards the first beam splitting device 104. A portion of the light passes through the first beam splitting device 104 and reaches the wavefront sensor 112 where the optical aberration of the light wavefront is detected. Furthermore, at the second beam splitting device 106 a portion of the light is redirected towards the detecting device 110, which for example may be an imaging device for capturing an image of the object 101 under observation, here the retina of an eye. When in operation, the adaptive optics system 100 in FIG. 1 corrects for time-varying aberrations between the object 101 and the wavefront sensor 112 by controlling the wavefront modifying device 108, and thus allows for improved imaging performance by the detecting device 110.

In the present embodiment, it may be assumed that light having the same wavelength is used both for detecting the optical aberration in the wavefront sensor 112 and for capturing an image in the detecting device 110. However, in an alternative embodiment, light of separate wavelengths may be used by the wavefront sensor 112 and the detecting device 110. In such an embodiment, a so called "cold mirror" can be used as the second beam splitting device 106 to reflect visible light, i.e. light having wavelengths between approximately 400 and 700 nm, towards the detecting device 110 while light having wavelengths above 700 nm is transmitted through the cold mirror towards the wavefront sensor 112. Furthermore, a so called "hot mirror" may be more suitable for use in other optical layouts or for other wavelength ranges.

Figure 2:
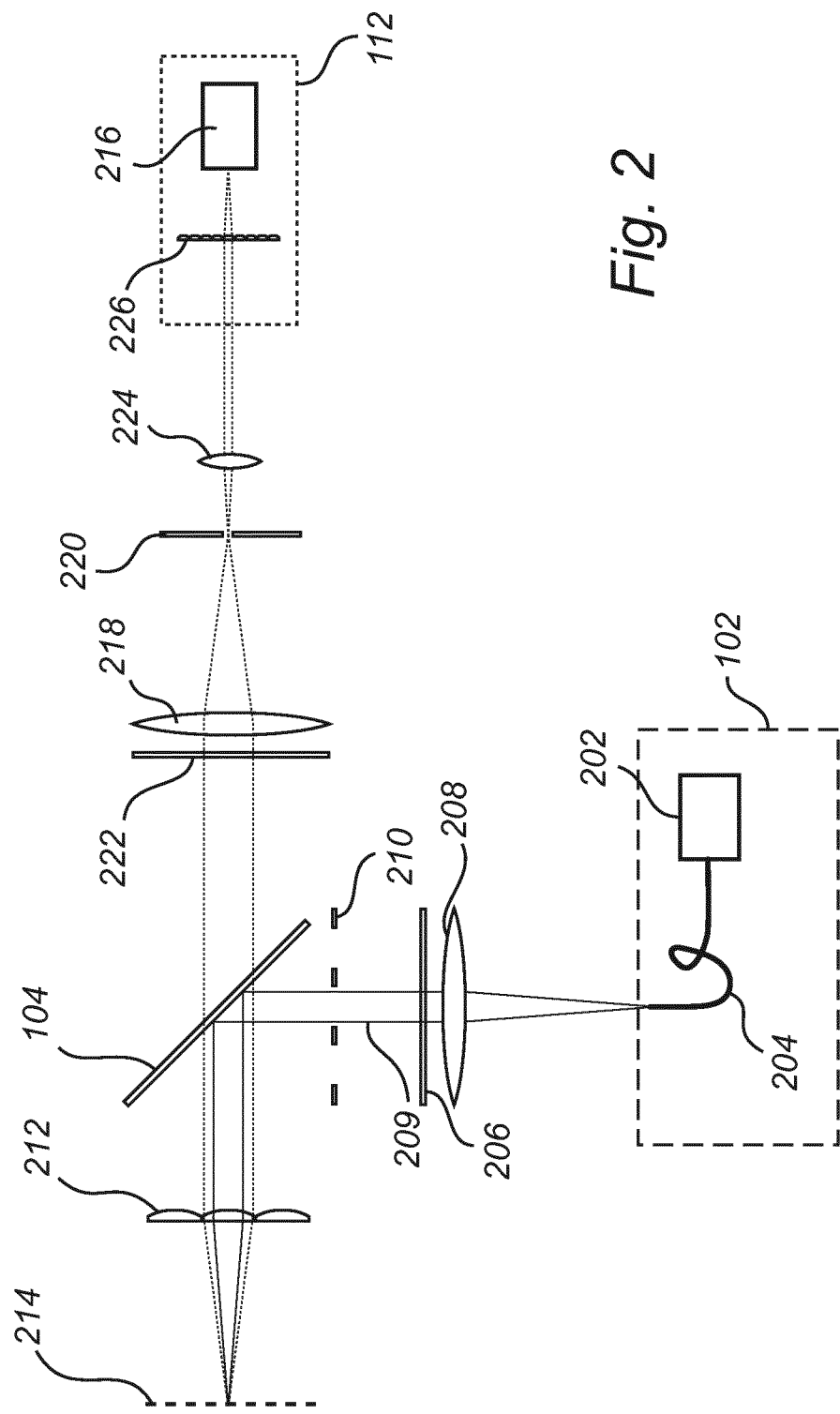
FIG. 2 schematically illustrates a portion of the optical system in FIG. 1 relating to the generation of guide star light beams according to an embodiment of the present invention.

FIG. 2 is a schematic illustration of the portions (120 in FIG. 1) of the adaptive optic system 100 relating to the generation of reference light beams and the propagation of light between the wavefront modifying device 108 and the wavefront sensor 112. Light formed by a light emitting device 202 such as a superluminescent diode is emitted from the end of an optical fiber 204, thus acting as a single point source. The light passes a collimating lens 208 so that a collimated light beam is created. Next, the emitted light passes a first polarizing filter 206, here a linear polarizing filter. Furthermore, a pupil mask 210 having a plurality of openings is inserted after the collimating lens 208, thereby forming a plurality of reference light beams according to the pattern of the openings in the pupil mask 210. The diameters of the light beams are thereby determined by the size of the openings in the pupil mask 210.

Furthermore, the pupil mask 210 reduces the amount of stray light as only the well defined reference light beams are allowed to pass the mask. For simplicity, only one reference light beam 209 is illustrated in FIG. 2. The polarizing filter 206 may alternatively be placed before the collimating lens 208 or after the pupil mask 210 without affecting the polarizing effect. The collimated reference light beams are then redirected by the beam splitter 104 so that a portion of the light propagates towards an optical element, here embodied as a collimating lens array (CLA) 212. The CLA 212 comprises a plurality of lenses arranged corresponding to the openings of the pinhole mask 210 so that reference light beams reaching the CLA 212 are focused to a plane 214 that is conjugate to the plane of the object 101. Conversely, reflected guide star light beams resulting from a reflection of the reference light beams at the object 101 are focused at the plane 214 and are collimated by the CLA 212. If another guide star geometry is preferred, the CLA 212 and/or the pupil mask 210 may simply by replaced so that another guide star pattern is produced. Furthermore, a desired guide star pattern may also be provided without the use of a pupil mask, in which case a single collimated light beam is divided into a plurality of reference light beams by the CLA 212.

Accordingly, light passing through the CLA 212 towards the object 101 is reflected at the object, in FIG. 2 represented by a conjugate object plane 214, after which the reflected guide star light beams propagate back along the same path through the CLA 212 where they are collimated.

A second polarizing filter 222 is arranged between the first beam splitting device 104 and the focusing lens 218. The second polarizing filter 222 is a linear polarizing filter rotated 90° in relation to the first polarizing filter 206. Hence, polarized reference light reflected by the CLA 212 in the direction towards the wavefront sensor 112 is blocked by the second polarizing filter 222. Thereby, light reflected by the CLA 212, which may be orders of magnitude stronger than the wavefront to be measured is prevented from reaching the wavefront sensor 112. The light reflected at the retina 101 can pass through the second polarizing filter 222 as a portion of the light reflected by the retina 101 becomes depolarized. It should be noted that the filtering effect may be achieved by other polarizing filter configurations than the aforementioned, by using e.g. circular polarizing filters. Furthermore, quarter-wave plate filters may be used to achieve the desired filtering effect for light reflected by objects which do not have a depolarizing effect.

Next, the portion of the light which passes through the first beam splitter 104 in the direction towards the wavefront sensor 112 reaches a second focusing lens 218. The second focusing lens 218 focuses the reflected guide star light beams to an opening in a field stop mask 220 in order to reduce the amount of stray light reaching the wavefront sensor 112.

After passing the field stop 220, the light beams pass through a second collimating lens 224 so that the wavefront reaching the lenslet array 226 of a Shack-Hartmann wavefront sensor 112 is collimated. The optical aberration of the light wavefront is detected at the imaging device 216 comprised in the wavefront sensor 112.

Figure 3A:
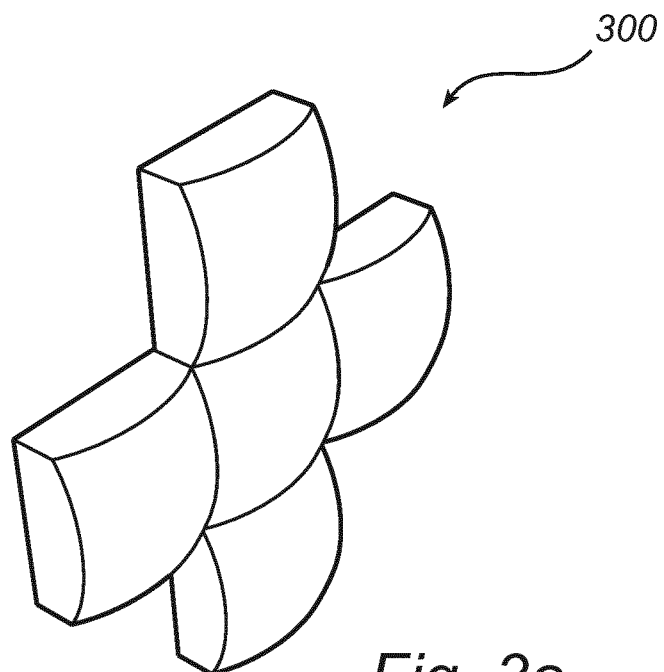
FIGS. 3a and 3b schematically illustrate optical elements according to embodiments of the present invention.
Figure 3B:
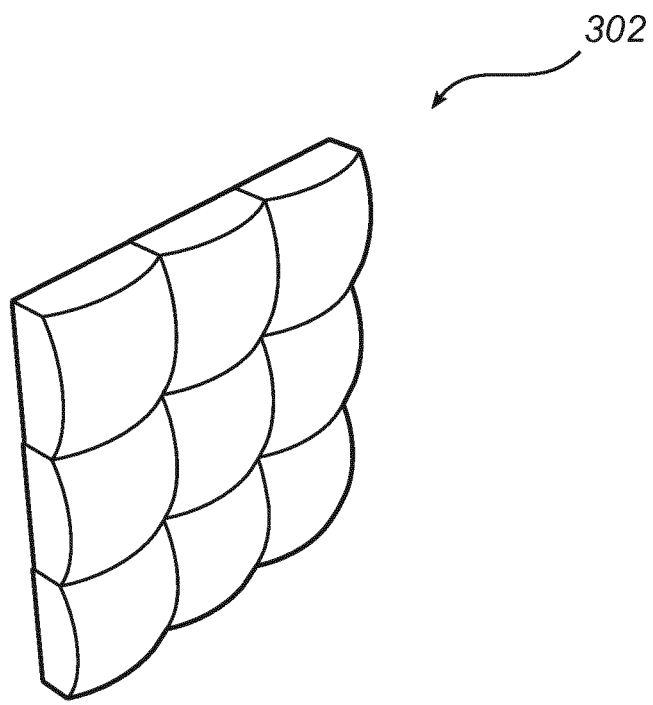

FIGS. 3a and 3b schematically illustrate two examples of different collimating lens arrays. The CLA may be made from a plurality of individual lenses 300 arranged in a desired pattern as illustrated in FIG. 3a, or the CLA may be made from one piece 302 shaped as a plurality of lenses as illustrated in FIG. 3b. The lenses can be made from various materials such as glass or optical plastic materials.

Even though the invention has been described with reference to specific exemplifying embodiments thereof, many different alterations, modifications and the like will become apparent for those skilled in the art.

Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. An optical system for detecting optical aberrations of light from an object, the optical system comprising:
   a reference light-source providing collimated reference light;
   an optical element configured to focus at least one collimated light beam incident on said optical element to a plurality of focal points in a conjugate object plane, said optical element being arranged in an optical path between said reference light-source and said object for receiving said reference light from said reference light-source, and transmitting said reference light as a plurality of reference light beams towards said object; and
   a wavefront sensor configured to detect a property indicative of an optical aberration of light incident on the wavefront sensor;
   wherein said optical element is further arranged to transmit a plurality of reflected guide star light beams resulting from reflection of said reference light beams at said object towards said wavefront sensor,
   wherein the reference light-source comprises a light emitting device and a first collimating lens for collimating the light provided by the light emitting device,
   wherein said light-emitting device is a point light-source arranged in a reference light-source plane,
   wherein said optical system further comprises:
   a focusing lens;
   a field stop; and
   a second collimating lens,
   wherein said focusing lens is arranged between the optical element and the wavefront sensor and configured to focus the plurality of reflected guide star light beams transmitted through the optical element to a focal point located at an opening of said field stop, wherein said second collimating lens is arranged between said field stop and said wavefront sensor and configured to collimate said reflected guide star light beams propagating from said opening in said field stop towards the wavefront sensor, and wherein the field stop is arranged in a conjugate reference light-source plane being a conjugate plane to said reference light-source plane.

2. The optical system according to claim 1, wherein the optical element is a phase modulating device.

3. The optical system according to claim 2, wherein the optical element is a collimating lens array.

4. The optical system according to claim 1, wherein the reference light-source further comprises a pupil mask comprising a plurality of openings configured to transform light from a light-source into a plurality of reference light beams.

5. An optical system for detecting optical aberrations of light from an object, the optical system comprising:

a reference light-source providing collimated reference light;

an optical element configured to focus at least one collimated light beam incident on said optical element to a plurality of focal points in a conjugate object plane, said optical element being arranged in an optical path between said reference light-source and said object for receiving said reference light from said reference light-source, and transmitting said reference light as a plurality of reference light beams towards said object; and a wavefront sensor configured to detect a property indicative of an optical aberration of light incident on the wavefront sensor;

wherein said optical element is further arranged to transmit a plurality of reflected guide star light beams resulting from reflection of said reference light beams at said object towards said wavefront sensor, wherein said optical system further comprises a light redirecting device arranged between the optical element and the wavefront sensor and configured to direct said collimated reference light from the reference light-source towards the optical element, and to allow passage of the reflected guide star light beams transmitted from the optical element towards the wavefront sensor, wherein said optical system further comprises a first polarizing filter arranged between said reference light-source and said light redirecting device such that light passing said first polarizing filter has a first polarization, and a second polarizing filter arranged between said light redirecting device and said wavefront sensor, wherein said second polarizing filter is configured so that passage of light having said first polarization is blocked.

6. The optical system according to claim 1, further comprising at least one wavefront modifying device arranged between said optical element and said object.

7. The optical system according to claim 6, wherein said at least one wavefront modifying device is a deformable mirror.

8. An adaptive optical system for compensating for optical aberrations comprising:

a control system;

an optical system according to claim 1 configured to provide an input signal to said control system corresponding to an optical aberration of received light detected by said optical system;

an image detecting device configured to provide an input to said control system;

a beam splitting device arranged between said optical system and an object, configured to redirect a portion of received light towards said image detecting device; and a wavefront modifying device controlled by said control system and arranged between said beam splitting device and said object;

wherein said control system is configured to control said wavefront modifying device based on said input signal from said optical system.

9. The optical system according to claim 5, further comprising at least one wavefront modifying device arranged between said optical element and said object.

10. The optical system according to claim 9, wherein said at least one wavefront modifying device is a deformable mirror.

11. An adaptive optical system for compensating for optical aberrations comprising:

a control system;

an optical system according to claim 9 configured to provide an input signal to said control system corresponding to an optical aberration of received light detected by said optical system;

an image detecting device configured to provide an input to said control system;

a beam splitting device arranged between said optical system and an object, configured to redirect a portion of received light towards said image detecting device; and a wavefront modifying device controlled by said control system and arranged between said beam splitting device and said object;

wherein said control system is configured to control said wavefront modifying device based on said input signal from said optical system.

* * * * *